(12) United States Patent
Mu

(10) Patent No.: US 11,814,796 B2
(45) Date of Patent: Nov. 14, 2023

(54) MANUFACTURING PROCESS OF INTERMITTENT COATING RELEASE PAPER

(71) Applicant: Foshan XinFei Hygiene Materials Co., Ltd., Foshan (CN)

(72) Inventor: Fanfei Mu, Foshan (CN)

(73) Assignee: Foshan XinFei Hygiene Materials Co., Ltd., Foshan (CN)

( * ) Notice: Subject to any disclaimer, the term of this patent is extended or adjusted under 35 U.S.C. 154(b) by 0 days.

(21) Appl. No.: 17/730,959

(22) Filed: Apr. 27, 2022

(65) Prior Publication Data

US 2022/0349126 A1 Nov. 3, 2022

(30) Foreign Application Priority Data

Apr. 30, 2021 (CN) .......................... 202110485622.8

(51) Int. Cl.
*D21H 27/00* (2006.01)
*D21H 19/32* (2006.01)
(Continued)

(52) U.S. Cl.
CPC ............. *D21H 27/001* (2013.01); *B05D 1/28* (2013.01); *D21H 19/32* (2013.01); *D21H 19/78* (2013.01);
(Continued)

(58) Field of Classification Search
CPC ........ B05D 1/28; B05D 7/50; B05D 2203/22; B05D 2518/10; D21H 27/001; D21H 19/32; D21H 19/78; D21H 19/824; D21H 23/30; A61F 13/15; A61F 13/15577; A61F 13/15764; B32B 37/12
(Continued)

(56) References Cited

U.S. PATENT DOCUMENTS 3,509,991 A * 5/1970 Hurst ....................... C09J 7/403
428/513
4,353,762 A * 10/1982 Bouda ............... A61F 13/15593
156/289
(Continued)

FOREIGN PATENT DOCUMENTS

CN 109762466 A * 5/2019

*Primary Examiner* — Brian K Talbot
(74) *Attorney, Agent, or Firm* — MORGAN, LEWIS & BOCKIUS LLP

(57) ABSTRACT

Disclosed is a manufacturing process of intermittent coating release paper, which includes: a) undercoating; b) primary drying in a drying oven; c) printing optical marks; d) coating silicon in a section; e) accurately coating heat-sealing material on front and back sides of the base material; f) secondary drying, rolling up, the action of coating the silicon and coating the heat sealing material is precisely positioned by using the optical marks printed in the previous process. The manufactured release paper can be directly applied to the packaging of women's sanitary napkins, pads, and maternity napkins, there is no need to use spaced release paper, the whole can be degraded or recycled for pulping, and can also reduce the use of various coating materials during production, reduce production costs, thus being beneficial to improve the production level of the existing process and the ecological environment protection.

8 Claims, 2 Drawing Sheets

(51) Int. Cl.
*D21H 19/78* (2006.01)
*D21H 19/82* (2006.01)
*D21H 23/30* (2006.01)
*B05D 1/28* (2006.01)
B05D 7/00 (2006.01)
A61F 13/15 (2006.01)
B32B 37/12 (2006.01)

(52) U.S. Cl.
CPC ........... *D21H 19/824* (2013.01); *D21H 23/30* (2013.01); *A61F 13/15* (2013.01); *A61F 13/15764* (2013.01); *B05D 7/50* (2013.01); *B05D 2203/22* (2013.01); *B05D 2518/10* (2013.01); *B32B 37/12* (2013.01)

(58) Field of Classification Search
USPC ........................................................ 427/288
See application file for complete search history.

(56) References Cited

U.S. PATENT DOCUMENTS

| | | | |
|---|---|---|---|
| 6,511,701 B1 * | 1/2003 | Divigalpitiya | B05D 1/28 427/407.1 |
| 9,248,057 B2 * | 2/2016 | Li | D21H 27/001 |
| 2009/0167013 A1 * | 7/2009 | Horikoshi | B41J 11/009 283/81 |
| 2014/0299253 A1 * | 10/2014 | Minamida | G01N 21/898 156/64 |

\* cited by examiner

MANUFACTURING PROCESS OF INTERMITTENT COATING RELEASE PAPER

CROSS-REFERENCE TO RELATED APPLICATIONS

This application claims priority to Chinese Utility Application No. CN 202110485622.8, filed Apr. 30, 2021. The disclosure of the application is incorporated herein for all purposes by reference in its entirety.

TECHNICAL FIELD

The present disclosure relates to the technical field of release paper manufacturing, and more particularly, to a manufacturing process of intermittent coating release paper.

BACKGROUND

Currently, sanitary napkins, sanitary pads, and maternity napkins are commonly accepted sanitary products by women. Well-known sanitary napkins, pads, and maternity napkins for women have an adhesive surface that sticks to the panties during use, so they need to be separated from the outer packaging film during packaging. The usual measure is to sandwich a layer of release paper between the adhesive surface and the packaging material to prevent the adhesive surface from sticking to the packaging material.

When in use, it is necessary to remove the outer packaging film first, and then tear off the release paper, which is inconvenient. Most of the packaging films are plastic products, which are not conducive to environmental protection. In addition, the existing product structure is relatively complex, the cost is high, and it is difficult to promote, especially in economically backward areas and vast rural areas. Furthermore, the same deficiencies exist in other similar products with self-adhesive surfaces.

If release paper is used as packaging material, the problem of material degradation can be solved to a certain extent. However, in the production of release paper, the release paper for heat-sealing packaging often needs to be fully coated with silicone oil, but in actual use, the heat-sealing area can be used without silicone oil, result in a large amount of release agent being wasted, and at the same time, cannot solve the problem that the brinks cannot be heat-sealed and packaged.

SUMMARY

In view of the technical defects existing in the background technology, the present disclosure proposes a manufacturing process of intermittent coating release paper, which solves the above-mentioned technical problems and satisfies the actual needs. The technical schemes are as follows:

A manufacturing process of intermittent coating release paper, which includes:
 a) undercoating, evenly coating an undercoat layer on one side of an unrolled base material;
 b) primary drying in a drying oven, drying the base material after the undercoating in a high-temperature drying oven;
 c) printing optical marks, feeding the base material between symmetrical upper and lower printing rollers, printing the optical marks at equal intervals, and ensuring that the optical marks are symmetrically distributed on both sides of the base material in the width direction;
 d) coating silicone oil in a section, enabling optical mark tracking, after identifying optical mark, waiting for a duration time t1, and coating silicone oil to the front of base material for a duration time t2, stopping coating silicone oil for a duration time t3 until the next identification to the optical mark, wherein t1=t3;
 e) accurately coating heat-sealing material on front and back sides of the base material, enabling the optical mark tracking, upon identifying optical mark, the action of coating heat-sealing material to the front and back sides of base material is performed for a duration time t1, then, the application of the heat-sealing material is stopped for a duration time t2, and the next action of coating the heat-sealing material on the front and back sides is performed for a duration time t3; and
 g) secondary drying, the base material after completing the above coating action enters a high-temperature suspension drying oven, and is dried in a non-contact manner, and then rolled up.

According to one of the further technical schemes of the present disclosure, a viscosity of the silicone oil for coating in the step d) is 170-300 mPa·s.

According to one of the further technical schemes of the present disclosure, in the step e), coating the glue is carried out by one glue feeding roller and one intermittent transfer coating roller, concave and convex surfaces of the intermittent roller are aligned to achieve precise pressing, and the precision is less than or equal to 0.1 μm, wherein the base material passes through a channel formed by the contacted intermittent rollers.

According to one of the further technical schemes of the present disclosure, the viscosity of the glue applied in the action of coating the heat-sealing material in the steps e) and f) is 30-50 mPa·s.

According to one of the further technical schemes of the present disclosure, coating the silicone oil in the step d) is carried out by a silicone oil coating mechanism composed of 3 or 4 silicone oil feeding rollers, one intermittent coating roller and one pressure-receiving roller, after the silicone oil feeding rollers are arranged in close contact with each other in sequence, one of them is arranged in close contact with the intermittent coating roller, and finally the pressure-receiving roller is arranged in contact with the intermittent coating roller, wherein, all the axes of the silicone oil feeding rollers are located in a straight line, the axes of the last one of the silicone oil feeding rollers, the pressure-receiving roller and the intermittent coating roller are located in another straight line, and two lines are perpendicular to each other.

According to one of the further technical schemes of the present disclosure, wherein the intermittent coating roller is driven by an optical mark tracking control electronic shaft.

According to one of the further technical schemes of the present disclosure, wherein a surface of the intermittent coating roller is provided with a hard colloidal material layer.

According to one of the further technical schemes of the present disclosure, the gram weight of the base material is in a range of 15-80 g/m2, and the tightness of the base material is in a range of 0.35-1 g/m3.

The beneficial effects that the present disclosure has are:
 1) The manufactured release paper can be directly used in small packages of sanitary napkins, pads, and maternity napkins, by using the self-contained release layer and heat-sealing layer, another release paper can be directly eliminated, and the whole is a fully degradable structure, which is more environmentally friendly;

2) Improving the coating process of the original heat sealing paper or release paper, the silicone oil no longer needs to be fully coated, and the utilization rate of the coating of the heat sealing material and the coating of the silicone oil on the paper surface reaches 100% without the problem of repeated coating, which saves at least half of the cost of coating materials;
3) At the same time, it can be used in release packaging materials with paper or film as the base material, the processed finished product has its own positioning optical mark, which will not only be conducive to cut during use, but also facilitate the subsequent precise printing process of the pattern on its surface, making the finished product packaging better and more convenient to use;
4) The intermittent release paper processed by the above process has solved the processing problem of the packaging structure of the side part, the finished product has good side heat sealing packaging performance, thereby meeting the needs of simplifying the packaging structure.

Figure 1:
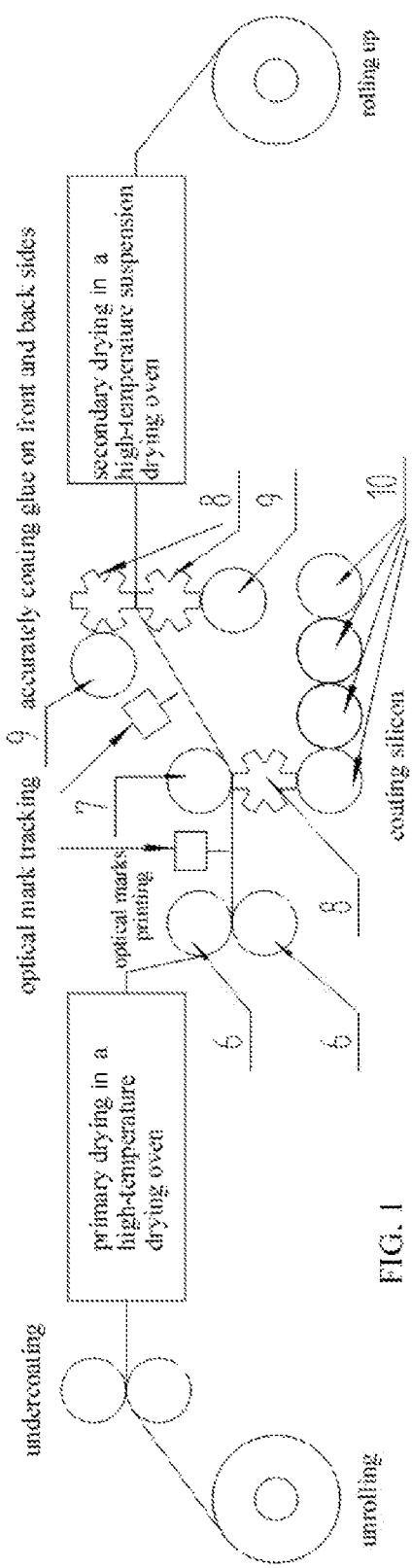
FIG. 1 is a process flow diagram of the present disclosure.

Reference numerals: base material 1, undercoat layer 2, optical mark 3, release layer 4, heat sealing layer 5, printing roller 6, pressure-receiving roller 7, intermittent coating roller 8, glue feeding roller 9, and silicone oil feeding roller 10.

DETAILED DESCRIPTION

Embodiments of the present disclosure will be described below with reference to the accompanying drawings and related embodiments. It should be pointed out that the following relevant embodiments are only preferred embodiments for better illustrating the present disclosure, the embodiments of the present disclosure are not limited to the following examples, in addition, the relevant necessary components known in the technical field, should be regarded as a well-known technology in the technical field, which can be known and mastered by those skilled in the technical field.

In the description of the present disclosure, it should be understood that, the orientation or positional relationship indicated by the terms "Landscape", "Up", "Down", "Front", "Back", "Left", "Right", "Vertical", "Horizontal", "Inside" etc. is based on the orientation or positional relationship shown in the drawings, it is only for the purpose of describing the disclosure and simplifying the description, not to indicate or imply that the device or element referred to must have a particular orientation, be constructed and operated in a particular orientation, and therefore should not be construed as limiting the disclosure.

Figure 2:
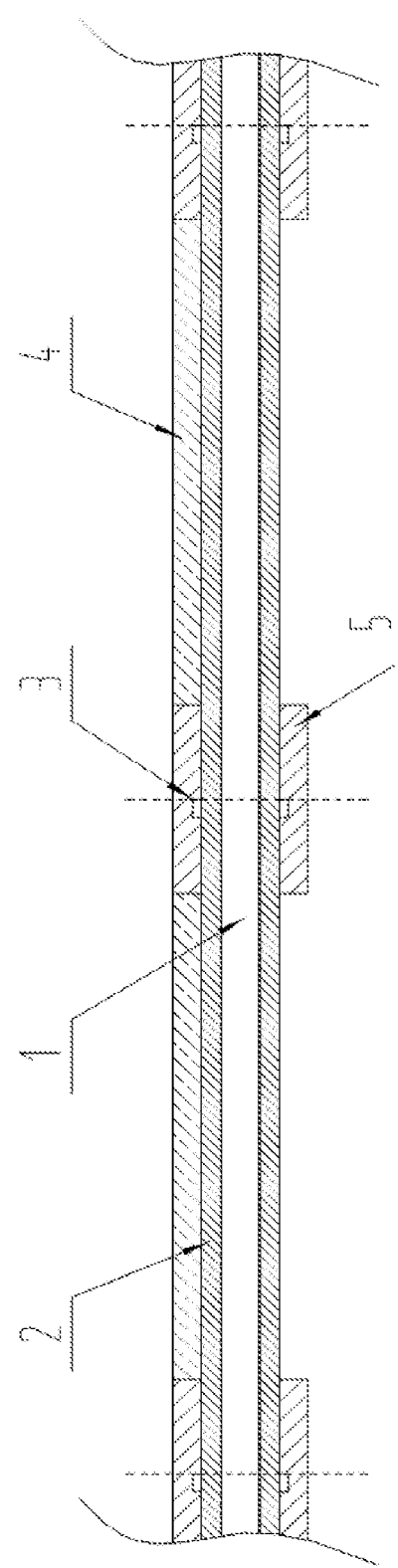
FIG. 2 is a cross-sectional structure diagram of the intermittent release paper manufactured by the present disclosure.

As shown in FIG. 1 and FIG. 2, a manufacturing process of intermittent coating release paper includes:

a) Undercoating, one side of the base material 1 after unrolling is evenly coated with the undercoat layer 2, wherein, the undercoat layer 2 is a base layer that must be fully coated before the release paper is coated with silicone oil or provided with the upper heat-sealing materials, which can make the bonding between the materials more closely.

b) Primary drying in a drying oven, the base material 1 after undercoating is dried in a high-temperature drying oven, and the base material 1 after undercoating should preferably be immediately entered into a high-temperature drying oven for drying, preferably a suspension type drying oven is used for drying, on the one hand, it can avoid the physical impact on the undercoated surface and ensure that the subsequent processing can be carried out smoothly, on the other hand, the drying efficiency of the suspension type drying oven is high, which is suitable for the high-speed operation of the entire assembly line, which ensures the production efficiency.

c) Printing optical marks, the base material 1 passes between the symmetrical upper and lower printing rollers 6, and the optical marks 3 are printed at equal intervals, and the optical marks 3 are symmetrically distributed on both sides of the base material 1 in the width direction, the length and width of the optical mark 3 are very small, and its thickness can be ignored, so it will not affect the coating of the release layer 4 and the adhesive layer, but it can provide an accurate positioning basis for the subsequent coating work, which is very convenient. When customers use this material, they can accurately locate the release area and the heat-sealing area according to the optical mark, so as to ensure that the glue-coated area of the sanitary products fits with the release area, and the heat-sealing seal of an equipment can be accurately pressed in the heat-sealing area.

d) Coating silicone oil in a section, optical mark 3 tracking is enabled, after identifying optical mark 3, waiting for a duration time t1, and coating silicone oil to the front of base material 1 for a duration time t2, stopping coating silicone oil for a duration time t3 until the next identification to the optical mark 3, wherein t1=t3. When t1=t3=0 s, it means that the silicone oil will be coated all the time. In order to achieve intermittent cutting, t1 and t3 need to be greater than 0, while time t2 controls the length variable of silicone oil smearing, that is, the length of the release layer 4.

Since optical mark 3 is the positioning basis for subsequent cutting or pattern printing, when t1=t3, the position of optical mark 3 is exactly located on the center line of the bonding area between two adjacent silicone oil surfaces/patterns, in this way, the release paper for packaging that is cut out will have a good heat-sealing structure/complete pattern.

e) Accurately coating heat-sealing material on front and back sides in a section, optical mark 3 tracking is enabled, and upon identifying optical mark 3, the action of coating heat-sealing material to the front and back sides of base material 1 is performed for a duration time t1, then, the application of the heat-sealing material is stopped for a duration time t2, and the next action of coating the heat-sealing material on the front and back sides is performed for a duration time t3.

The area where the heat-sealing material is coated is between the adjacent silicone oil-coated areas, that is, the release layers 4, and a heat-sealing layer 5, which is used for the heat-sealing structure required for packaging, is formed. Due to the positioning of the optical mark 3, the area of the coated heat-sealing material can be accurately spaced from the release area, ensuring the uniformity and integrity of the heat-sealing layer 5, and saving the amount of the silicone oil to be applied. The operation of coating the heat-sealing material area can make the heat-sealing structure more stable, and the symmetrical arrangement of the two heat-sealing layers 5 on both sides of the base material is also conducive to the integrity of the structure and ease of use, while avoiding material waste.

f) Secondary drying, the base material 1, after completing the above coating action, enters the high temperature suspension drying oven, and after drying in a non-contact manner, it is rolled up, it is preferable to enter the high-temperature suspension drying oven for drying immediately after all the feeding processes are completed, so as to avoid physical damage to the paper surface and lead to the generation of waste products.

According to one of the further technical schemes of the present disclosure, the viscosity of the silicone oil to be coated in the silicone oil-coating action of the step d) is 170-300 mPa·s, and the silicone oil with this viscosity does not volatilize solvent substances, the amounts of the silicone oil can be precisely adjusted by a 6-roll mechanism, so as to meet the coating amount required by customers. Moreover, the silicone oil with this viscosity has the adaptability of the release paper feeding speed of 200-400 m/min, and this speed range is the preferred speed range for the production of intermittent release paper, and it is also a widely used process parameter. The quality and precision of the products manufactured at a speed of 200 m/min are the best, while a speed of 400 m/min can still maintain better product quality when the output is doubled, similar effects cannot be achieved if silicone oils with other viscosities are used, and the silicone oils with this viscosity do not need to be diluted with solvents, which are not easy to cause solvent residues, thereby being safer, and meeting the requirements of environmental protection.

According to one of the further technical schemes of the present disclosure, the action of coating the heat-sealing material in the step e) is executed by one glue feeding roller and one intermittent transfer coating roller at one side, the concave and convex surfaces of the intermittent roller are neat and aligned to achieve precise pressing, and the precision is less than or equal to 0.1 μm, wherein the base material passes through a channel formed by the contacted intermittent rollers.

The intermittent coating roller 8 is a coating mechanism with intermittent coating surfaces, and the arc length between the intermittent surface represents the length of the feeding material, the intermittent surface of the intermittent coating roller 8 is made of a hard colloidal material with a shore hardness of 85, for the colloidal material with this hardness, the main raw material is PU glue, compared with the commonly used glue rollers with shore hardness of 60-70 in the prior art, it is more suitable for heat-sealing coating liquid materials with a wider range of concentration, and can also adapt to silicone oil with a large viscosity, the coating roller wrapped with the glue material under this hardness can provide better transfer performance, so that the coated glue layer material can be used to the maximum extent, it is beneficial to the formation of the release layer 4 of the silicone oil and the heat sealing layer 5 on the surface of the base material 1, which reduces the waste of materials and reduces the difficulty of cleaning during maintenance.

The length of the intermittent surface can be customized according to actual needs, so that the intermittent coating roller 8 can be customized, wherein, the accuracy must be no more than 1 micron to meet the production of intermittent release paper of different specifications. Similarly, the feeding method of the intermittent coating roller 8 can also be used for other materials that require intermittent coating. The coating of the intermittent coating roller 8 can be carried by itself or supplied in other forms of feeding.

According to one of the further technical schemes of the present disclosure, the viscosity of the glue coated in the action of coating the heat-sealing material in the step e) is 30-50 mPa·s, this kind of heat sealing material is preferably a mixture of food-grade silk protein aqueous scheme and polyhydroxy compound, which can not only meet the bonding requirements, but also can be completely degraded and can be fully degraded according to customer requirements, by adjusting the formula and coating amount, the heat-sealing layer structure with the heat-sealing strength of 0.5-15 N/15 mm is provided, thereby being suitable for packaging papers with different packaging and use needs, especially small personal absorbent products such as sanitary napkins, maternity napkins, nursing pads, etc., this kind of the product often has special requirements for the timing of use, so it must be well packaged, and the packaging paper needs to be easy to separate from the product.

According to one of the further technical schemes of the present disclosure, the silicone oil coating action of the step d) is carried out by a silicone oil coating mechanism composed of 3 or 4 silicone oil feeding rollers 10, one intermittent coating roller 8 and one pressure-receiving roller 7, after the silicone oil feeding rollers 10 are arranged in close contact with each other in turn, one of them is then arranged in close contact with the intermittent coating roller 8, finally, the pressure-receiving roller 7 is arranged in contact with the intermittent coating roller 8, all the axes of the silicone oil feeding rollers 10 are located in a straight line, and the axes of the last silicone oil feeding roller 10 and the pressure-receiving roller 7 and the intermittent coating roller 8 are located in another straight line, the above-mentioned two different axes-connecting lines are perpendicular to each other.

The five-rollers or six-rollers structure can ensure the accuracy and uniformity of the silicone oil coating, especially the formation of the release layer 4 is of great significance to the packaged object, the intermittent coating can maximize the use of the release layer 4, and avoid the overlap of the release layer 4 and the heat sealing layer 5, thereby reducing the waste of materials, this structure can precisely control the amount of silicone oil within the range of 0.3-1.5 g/m2, and the more the rollers, the higher the coating accuracy, thereby reducing the waste of silicone oil and saving costs.

According to one of the further technical schemes of the present disclosure, the intermittent coating roller 8 is driven by an optical mark tracking control shaft to ensure that the intermittent coating can be accurately implemented by the optical mark 3, so as to realize accurate coating.

According to one of the further technical schemes of the present disclosure, the surface of the intermittent coating roller 8 is provided with a hard colloidal material layer with a Shore hardness of 85 degrees. Because the viscosity of silicone oil as a release agent is 170~300 mPa·s, the viscosity of the heat-sealing material is 30-50 mPa·s, and the solid content and viscosity of the coating materials are different, which will cause inconsistent leveling and require high roller surface treatment, the roller with concave and convex surfaces is coated with colloidal material, and the surface of the coating roller with higher hardness will not be affected by material viscosity and speed changes, the coating liquid is evenly stabilized on the roller to ensure the accuracy of coating, and cost and durability also need to be considered, therefore, the use of PU glue-based colloidal materials can better meet the needs.

According to one of the further technical schemes of the present disclosure, the gram weight of the base material 1 is selected in the range of 15-80 g/m2, and the tightness is selected in the range of 0.35-1 g/m3, the base material 1 has the most commonly used gram weight range and tightness range in packaging, which can meet the needs of packaging.

The beneficial effects that the present disclosure has are:
1) The manufactured release paper can be directly used in small packages of sanitary napkins, pads, and maternity napkins, by using the self-contained release layer and heat-sealing layer, the use of additional release paper can be directly eliminated, and the whole is a fully degradable structure, which can be recycled for pulping, which is more environmentally friendly;
2) Improving the coating process of the original heat sealing paper or release paper, silicone oil no longer needs to be fully coated, and the utilization rate of the coating of the heat sealing material and the coating of the silicone oil on the paper surface reaches 100% without the problem of repeated coating, which saves at least half of the cost of coating materials;
3) At the same time, it can be used in release packaging materials with paper or film as the base material, the processed finished product has its own positioning optical mark, which can not only be conducive to cut during use, but also facilitate the subsequent precise printing process of the pattern on its surface, making the finished product packaging better and more convenient to use; and
4) The intermittent release paper processed by the above process has solved the processing problem of the side portion of the packaging structure, the finished product has good side heat sealing packaging performance, thereby meeting the needs of simplifying the packaging structure.

The above are only the preferred embodiments of the present disclosure, it should be pointed out that for those skilled in the art, without departing from the principle of the present disclosure, several improvements and modifications can also be made, and these improvements and modifications should also be regarded as the protection scope of the present disclosure.

What is claimed is:

1. A manufacturing process of intermittent coating release paper, comprising steps of:
    a) undercoating, wherein an undercoat layer is coated on two sides of an unrolled base material;
    b) primary drying in a drying oven, wherein drying the base material after the undercoating in a first drying oven;
    c) printing optical marks, wherein the base material passes between symmetrical upper and lower printing rollers, printing the optical marks at equal intervals, and wherein the optical marks are symmetrically distributed on both sides of the base material in the width direction;
    d) coating silicone oil in a section, wherein enabling optical mark tracking, after identifying optical mark, waiting for a duration time t1, and coating the silicone oil to a surface of base material for a duration time t2, and stopping coating silicone oil for a duration time t3 until the next identification to the optical mark, wherein t1=t3;
    e) accurately coating heat-sealing material on front and back sides of the base material in a section, wherein enabling the optical mark tracking, upon identifying the optical mark, the action of coating heat-sealing material to the front and back sides of base material is performed for a duration time t1, then stopping the application of the heat-sealing material for a duration time t2, and the next action of coating the heat-sealing material on the front and back sides is performed for a duration time t3;
    f) secondary drying, wherein the base material after coating heat-sealing material enters into a second drying oven, and is dried in a non-contact manner and then rolled up.

2. The manufacturing process of intermittent coating release paper of claim 1, wherein, a viscosity of the silicone oil for coating in the step d) is 170-300 mPa·s.

3. The manufacturing process of intermittent coating release paper of claim 1, wherein, in the step e), coating the heat-sealing material on the front and back sides is carried out by one glue feeding roller and one intermittent transfer coating roller, concave and convex surfaces of the intermittent roller are aligned to achieve precise pressing, and the precision is less than or equal to 0.1 μm, wherein the base material passes through a channel formed by the contacted intermittent rollers.

4. The manufacturing process of intermittent coating release paper of claim 3, wherein a viscosity of the heat-sealing material for coating in the step e) is 30-50 mPa·s.

5. The manufacturing process of intermittent coating release paper of claim 1, wherein, coating silicone oil in the step d) is carried out by a silicone oil coating mechanism composed of 3 or 4 silicone oil feeding rollers, one intermittent coating roller and one pressure-receiving roller, after the silicone oil feeding rollers are arranged in close contact with each other in sequence, one of them is arranged in close contact with the intermittent coating roller, and finally the pressure-receiving roller is arranged in contact with the intermittent coating roller, wherein, all the axes of the silicone oil feeding rollers are located in a straight line, the axes of the last one of the silicone oil feeding rollers, the pressure-receiving roller and the intermittent coating roller are located in another straight line, and two lines are perpendicular to each other.

6. The manufacturing process of intermittent coating release paper of claim 5, wherein the intermittent coating roller is driven by an optical mark tracking control electronic shaft.

7. The manufacturing process of intermittent coating release paper of claim 5, wherein a surface of the intermittent coating roller is provided with a colloidal material layer.

8. The manufacturing process of intermittent coating release paper of claim 1, wherein, a gram weight of the base material is in a range of 15-80 g/m$^2$, and a tightness of the base material is in a range of 0.35-1 g/m$^3$.

* * * * *